(12) United States Patent
Albert et al.

(10) Patent No.: US 11,339,114 B2
(45) Date of Patent: *May 24, 2022

(54) OPHTHALMIC COMPOSITION CONTAINING COMPOUNDS FOUND IN HARDERIAN GLAND SECRETIONS

(71) Applicant: RestorTears, LLC, Madison, WI (US)

(72) Inventors: Daniel M. Albert, Madison, WI (US); Arthur S. Polans, Madison, WI (US)

(73) Assignee: RestorTears, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,305

(22) Filed: May 21, 2018

(65) Prior Publication Data

US 2018/0265450 A1 Sep. 20, 2018

Related U.S. Application Data

(60) Continuation of application No. 15/051,092, filed on Feb. 23, 2016, now Pat. No. 9,994,511, which is a division of application No. 14/523,264, filed on Oct. 24, 2014, now Pat. No. 9,289,494.

(60) Provisional application No. 61/906,487, filed on Nov. 20, 2013.

(51) Int. Cl.
| | | |
|---|---|---|
| *C07C 69/708* | (2006.01) | |
| *C07C 69/28* | (2006.01) | |
| *C07C 69/593* | (2006.01) | |
| *A61K 45/06* | (2006.01) | |
| *A61K 9/00* | (2006.01) | |
| *A61K 31/22* | (2006.01) | |
| *A61K 31/225* | (2006.01) | |

(52) U.S. Cl.
CPC .......... *C07C 69/708* (2013.01); *A61K 9/0048* (2013.01); *A61K 31/22* (2013.01); *A61K 31/225* (2013.01); *A61K 45/06* (2013.01); *C07C 69/28* (2013.01); *C07C 69/593* (2013.01)

(58) Field of Classification Search
CPC ..... C07C 69/708; C07C 69/28; C07C 69/593; A61K 9/0048; A61K 31/22; A61K 31/225; A61K 45/06
USPC ...................................................... 514/547
See application file for complete search history.

(56) References Cited

U.S. PATENT DOCUMENTS

| | | |
|---|---|---|
| 4,595,681 A | 6/1986 | Snyder |
| 6,348,496 B1 | 2/2002 | Belanger |
| 7,223,737 B1 | 5/2007 | Ke et al. |
| 7,745,461 B1 | 6/2010 | Klimko |
| 2002/0002185 A1 | 1/2002 | Reed |
| 2003/0109488 A1 | 6/2003 | Yanni et al. |
| 2004/0157805 A1 | 8/2004 | Belanger et al. |
| 2006/0058375 A1 | 3/2006 | Klimko et al. |
| 2006/0069075 A1 | 3/2006 | Gamache et al. |
| 2006/0128803 A1 | 6/2006 | Klimko et al. |
| 2007/0082017 A1 | 4/2007 | Tseng |
| 2008/0009437 A1 | 1/2008 | Xia et al. |
| 2008/0305994 A1 | 12/2008 | Zhang et al. |
| 2009/0253804 A1 | 10/2009 | Marcy et al. |
| 2012/0301464 A1 | 11/2012 | Friedman et al. |
| 2013/0090308 A1 | 4/2013 | Vehige et al. |
| 2013/0172297 A1 | 7/2013 | Shichijo et al. |
| 2013/0295206 A1 | 11/2013 | Gore et al. |

OTHER PUBLICATIONS

Schneditz. Influence of tonicity on the viscoelastic properties of blood during isovolemic dilution. Basic Res. Cardiol. 82: 388-395.*
De Lederkremer et al. Hexadecylpalmitoylglycerol or ceramide is linked to similar glycophosphoinositol anchor-like structures in Trypanosoma cruzi. Eur. J. Biochem. 218, 929-936. 1993.*
Gradman et al. Combination therapy in hypertension. Journal of American Society of Hypertension, 4(2), 2010, 90-98.
Mankidy, et al. Membrane plasmalogen composition and cellular cholesterol regulation: a structure activity study, Lipids in Health and Disease, 2010, 9:62, pp. 1-17.
CN Office Action, CN Patent Application No. 201480063754.X, dated Apr. 17, 2018.
Salto et al. "Chemo-enzymatic synthesis of 1-O-hexadecyl-2-O-palmitoyl-sn-glycerol" Biotechnology Letters, vol. 19, No. 9, Sep. 1997, pp. 853-855.

* cited by examiner

*Primary Examiner* — Yevgeny Valenrod
(74) *Attorney, Agent, or Firm* — Casimir Jones S.C.; J. Mitchell Jones

(57) ABSTRACT

The present invention is directed to pharmaceutical compositions comprising compounds found in Harderian gland secretions, a method of treating dry eye in a human comprising ophthalmically administering an effective amount of a compound, e.g. a lipid compound, found in Harderian gland secretions, pharmaceutical compositions comprising said lipid compounds, as identified by characteristic chemical data and mass spectra of said lipid compounds, said lipid compound in essentially pure form, and an ophthalmic vehicle comprising a therapeutic agent and a compound present in the secretions of the Harderian gland, e.g. a lipid compound, found in the secretions of the Harderian gland, e.g. a rabbit Harderian gland.

2 Claims, 5 Drawing Sheets

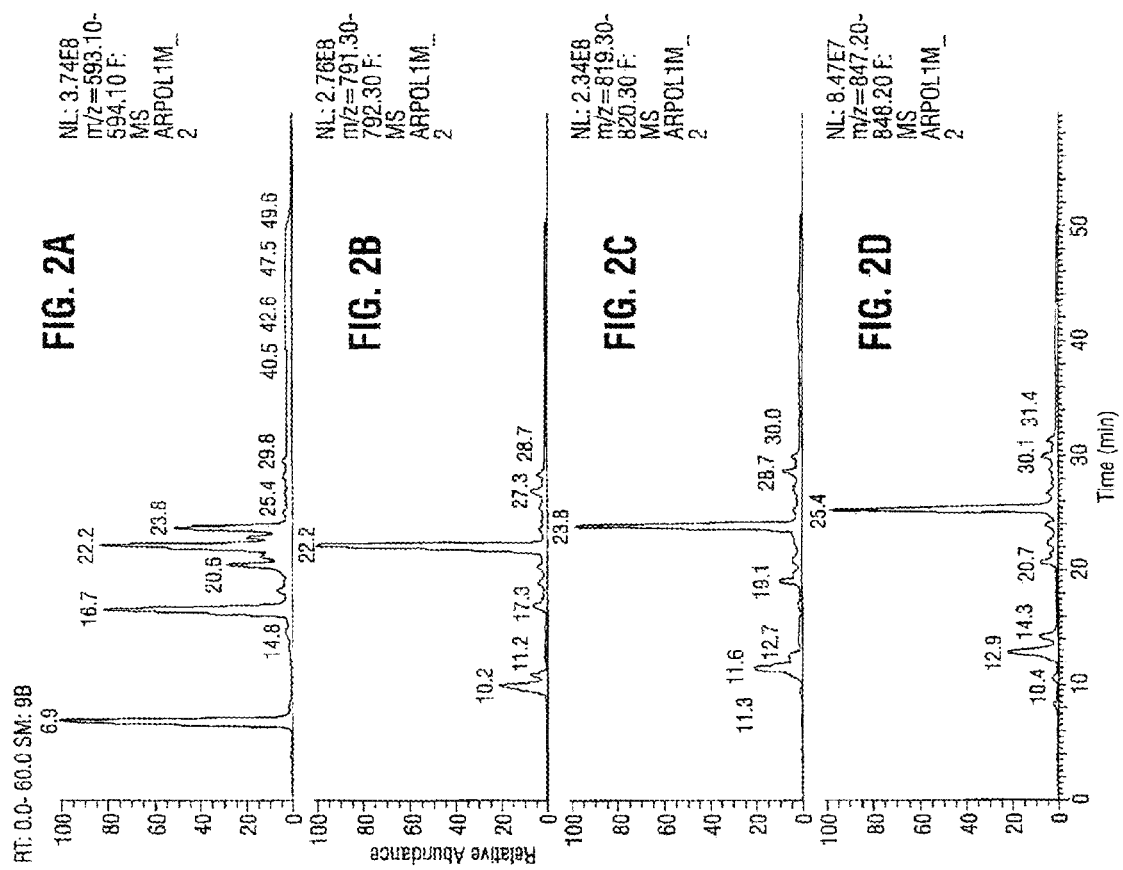

OPHTHALMIC COMPOSITION CONTAINING COMPOUNDS FOUND IN HARDERIAN GLAND SECRETIONS

CROSS-REFERENCE TO RELATED APPLICATIONS

This application is a continuation of U.S. patent application Ser. No. 15/051,092, filed Feb. 23, 2016, which is a divisional of U.S. patent application Ser. No. 14/523,264, filed Oct. 24, 2014, now U.S. Pat. No. 9,289,494, which claims the benefit of U.S. Prov. Appl. 61/906,487, filed Nov. 20, 2013, each of which is incorporated by reference in its entirety.

BACKGROUND OF THE INVENTION

1. Field of Invention

The present invention relates to the use of compounds which are present in the secretions of the Harderian glands of certain animals, e.g. rabbits, in the preparation of a medicament for treating "dry eye" or other ocular disorders. A further embodiment of the present invention relates to a method of treating a patient suffering from "dry eye" and related ocular disorders with said medicament.

2. Description of Related Art

The Harderian gland is a gland found within the eye's orbit which occurs in vertebrates (reptiles, amphibians, birds and mammals) that possess a nictitating membrane. The gland secretes fluid (mucous, serous or lipid) that varies between different groups of animals. Various reptiles, birds, and sharks, as well as mammals such as camels and polar bears, have a full nictitating membrane. It is often called a third eyelid. In many mammals, there is a small vestigial remnant of the nictitating membrane present in the corner of the eye. In some animals it acts as an accessory to the lacrimal gland, secreting fluid that eases movement of the nictitating membrane. The gland may have several other functions, including that of a photoprotective organ, a location of immune response, a source of thermoregulatory lipids, a source of pheromones, a source of saliva, and/or a site of osmoregulation.

The Harderian gland in rabbits is related to the nictitating membrane (from Latin nictare, to blink), which is a transparent or translucent third eyelid present in some animals that can be drawn across the eye for protection and to moisten the eye while also maintaining visibility. In rabbits and rodents, the Harderian gland secrets non-polar lipids near the surface of the eye which mixed with the tears of the lacrimal gland. Rabbits do not suffer from "dry eye" as do humans. It is believed to be the lack of protective fluids of the Harderian gland may make humans more susceptible to "dry eye" and diseases associated with "dry eye.

Humans are subject to the development of damage to the cornea and conjunctiva as a result of insufficient tears or insufficient lubricating substances within the tears. This is a common problem increasing with age and more marked in women than men. Various wetting agents and solutions commonly known as "artificial tears" are only partially effective in protecting tissues in patients with "dry eyes". Alteration, deficiency or absence of the tear film may lead to intractable desiccation of the corneal epithelium, ulceration and perforation of the cornea, an increased incidence of infectious disease, and ultimately, severe visual impairment and blindness.

Dry eye is a disease of the tears and ocular surface resulting in symptoms of discomfort, visual disturbance, and a tear film that inadequately protects the eye leaving potentially damaging conditions for the ocular surface. Keratoconjunctivitis is inflammation of the cornea and conjunctiva. Keratoconjunctivitis sicca (KCS) is chronic, bilateral desiccation of the conjunctiva and cornea due to an inadequate tear film.

Individuals suffering from tear film dysfunctions are diagnosed with keratoconjunctivitis (KCS), for example Sjögren's Syndrome or simply "dry eye". These lacrimal abnormalities are subdivided into four general categories:
1. Aqueous tear deficiencies most frequently responsible for dry eye states, originating from lacirmal gland disorders including autoimmune disease, congenital alacrima, paralytic hyposecretion or excretory duct obstruction.
2. Mucin deficiency which is observed in conditions associated with trachoma, thermal and chemical burns, hypovitaminosis A.
3. Lipid abnormalities.
4. Diminished eyelid function. (See U.S. Pat. No. 6,107, 289).

Evaporative keratoconjunctivitis sicca is caused by loss of the tear film due to abnormally rapid evaporation which is a result of an inadequate oil layer on the surface of the aqueous layer of tears. Symptoms may result from an abnormal oil in the tear film.

Aqueous tear-deficient keratoconjunctivitis sicca is caused by inadequate tear volume while evaporative keratoconjunctivitis sicca (more common) is caused by accelerated tear evaporation due to poor tear quality. Aqueous tear-deficient keratoconjunctivitis sicca is most commonly an isolated idiopathic condition in postmenopausal women. It is also commonly part of Sjögren's syndrome. It is secondary to other conditions that scar the lacrimal ducts due to trachoma. It may result from a damaged or malfunctioning lacrimal gland, HIV (diffuse infiltrative lymphocytosis syndrome), local radiation therapy, or familial dysautonomia. A subset of the dryness symptoms is expressed as Sjögren's syndrome, which is also a known "Sicca syndrome" and is a systemic autoimmune disease in which immune cells attack and destroy the exocrine glands that produce tears and saliva. Nine out of ten Sjögren's patients are women and the average age of onset is late 40s, although Sjögren's occurs in all age groups in both women and men. It is the second most common autoimmune rheumatic disease in the United States. Autoimmune rheumatic disorders include Rheumatoid arthritis A.

Patients suffering from dry eye report itching; burning; a gritty, pulling, or foreign body sensation; or photophobia. A sharp stabbing pain, eye strain or fatigue, and blurred vision may also occur. Some patients note a flood of tears after severe irritation.

Artificial tears are used to relieve temporarily the symptoms of discomfort associated with dry eye and sometimes blocking the nasolacrimal openings. Ideally the artificial tear or lubricant should provide lubrication and moisture to the tear film and protect the ocular surface.

Prior art compositions useful for administering medications into the eyes are generally effective, but many have the drawback of requiring frequent administration and are often rapidly washed away by the natural processes of the eye. The current prescribed therapeutic approach to managing KCS is the frequent application of artificial tear substitutes for lubricating the anterior eye surface. Frequent artificial tears and lubricants may cause visual blurring and alter the ocular surface and chemistry of the tear film on the ocular surface.

Hypotonic solutions used for ocular irritation may flood the ocular surface with water, enter the cells and produce a hypotonic artificial tear, which may leave the ocular surface with less water and more irritated than before application of the solution. Glycerol is a common osmotic agent and a humectant and ophthalmic lubricant. It is applied to the ocular surface to relieve irritation at concentrations of approximately 1%. Excessive addition of glycerol to the human eye may not provide extended benefits for ocular lubrication. A long term ophthalmic lubricant or vehicle, to protect the tear film and ocular surface is needed. The present invention discloses a method of treating "dry eye" with compounds found in Harderian gland secretions.

SUMMARY OF THE INVENTION

New compositions which utilize compounds present in Harderian gland secretions and a method of treating dry eye in a human in need thereof comprising opthalmically administering an effective amount of a compound present in Harderian gland secretions are disclosed herein.

In particular, the present invention relates to a method of treating dry eye, in a human in need thereof, comprising opthalmically administering an effective amount of a compound present in the Harderian gland secretions of rabbits.

Broadly, the present invention is directed to pharmaceutical compositions comprising compounds found in Harderian gland secretions, a method of treating dry eye in a human comprising ophthalmically administering an effective amount of a compound, e.g., a lipid compound, found in Harderian gland secretions, pharmaceutical compositions comprising said lipid compounds, as identified by characteristic chemical data and mass spectra of said lipid compounds, said lipid compound in essentially pure form, and an ophthalmic vehicle comprising a therapeutic agent and a compound present in the secretions of the Harderian gland, e.g. a lipid compound, found in the secretions of the Harderian gland, e.g., a rabbit Harderian gland.

Thus, the present invention includes a method of treating dry eye in a human comprising ophthalmically administering an effective amount of a lipid compound, found or present in the secretions of the Harderian gland.

The present invention further includes a pharmaceutical composition comprising a lipid compound, identified in the secretions of the Harderian gland, e.g., a rabbit Harderian gland.

The present invention further includes a compound identified by certain characteristic chemical data and mass spectra of the lipid compound(s) found in the secretions of the Harderian gland in its essentially pure form.

The present invention further includes an ophthalmic vehicle comprising said Harderian lipid compound.

A further embodiment of the present invention relates to a method of treating a patient suffering from "dry eye" and related ocular disorders to provide improved stability of the tear film of said patient with said pharmaceutical composition or vehicle.

The present invention discloses new compositions related to the Harderian gland secretions and a method for using such compositions to effectively administer therapeutic components to the eyes of a patient suffering from an ocular disorder or disease.

The present invention may be employed in methods which comprise administering the composition to a cornea of an eye, for example, contacting the composition with the cornea of the eye to prevent or alleviate ocular disorders or conditions.

The present invention includes one or more lipid compounds from the Harderian gland secretions effective, as a delivery vehicle to improve administration of medicaments to the human eye by improving the tear film when mixed on the eye with tear fluid of a human with "dry eye" symptoms.

Alternatively, the lipid compound may be used to wet the dermal portion of the eyelid of a human eye after the composition is administered to the human eye. For example, the present compositions may be effective to wet a portion of the eyelid that is the junction between the conjunctiva mucus membrane tissue and the dermis of the eyelid.

The overall higher molecular weight of the lipid compound from the rabbit Harderian tear secretions compared to the tear secretions of the human provides, for example, an increased retention of the therapeutic component on the cornea and into the eye.

Each of the lipid compounds obtained from the secretions of the Harderian gland has a different molecular weight resulting from variations on the saturated or unsaturated alkyl or alkenyl chains present in said lipid compound. The multiple alkyl and alkenyl chain chemistry of the lipid compounds includes one or more structural component portions, for example, having from 5 to 30 carbon atoms. Average molecular weights of the identified, saturated and unsaturated compounds which are components of the lipid compositions of the invention may be about 500 amu or less.

In one very useful embodiment, the lipid compounds include a first ether ester component portion having a first molecular weight, and a second ether ester component having a second, different, molecular weight. Preferably, the lipid compounds include five ether ester component portions having different molecular weights. Advantageously, each of the ether ester component portions may be present in an amount effective to provide a pharmaceutical composition having an enhanced delivery of a therapeutic component to a patient, for example, when administered to a cornea of a patient, relative to a substantially identical composition with no lipid compound.

Any suitable Harderian lipid compound may employed in accordance with the present invention. Such lipid compound should be ophthalmically acceptable and compatible with the other components of the composition, and effective, in ophthalmically reasonable concentrations, to facilitate administration of a therapeutic component to a patient when administered to an eye of the patient and to otherwise function in accordance with the present invention.

In another useful embodiment, the present lipid compounds may be used as a delivery vehicle for any suitable therapeutic component.

Advantageously, the therapeutic components in the present Harderian lipid compound-containing vehicle are compatible with ocular tissue, and ophthalmically acceptable.

The therapeutic component is selected to provide a desired therapeutic effect to the eye and/or to another body part and/or systemically to the human or animal to whom the present composition is administered.

Additionally, because the lipid compound provides a vehicle for the therapeutic medicament administered to the eye to actually pass through, or penetrate the cornea, rather than being washed away by the natural processes of the eye, the present compositions may include a reduced quantity of the therapeutic component in a composition to obtain a given therapeutic effect relative to a substantially identical composition having no Harderian lipid compound. In general, the present compositions provide for more effective utilization of the therapeutic component relative to substantially identical compositions having no Harderian secretion compounds. The vehicle or carrier component is ophthalmically acceptable and may include one or more lipid components which are effective in providing such ophthalmic acceptability and/or otherwise benefitting the composition and/or the eye to which the composition is administered and/or the patient whose eye the composition is administered to.

In addition to being useful for administering therapeutic components to a the eye of a patient, or to a patient through the eye of the patient, the present compositions can be effective to provide lubrication to an eye when administered to the eye, in the absence of a therapeutic component for example, when administered to the human or animal eye as an artificial tear.

Methods of producing the present compositions include combining the Harderian secretions and/or lipid compounds with an ophthalmically acceptable carrier component and, if desired, the therapeutic component.

The present invention includes a Harderian lipid compound as an ophthalmically acceptable vehicle component for delivering an effective amount of therapeutic medicaments to the eye. The invention features a new approach to managing keratoconjunctivitis sicca (KCS), dry eye, or Sjogren's syndrome by topical application to the eye of a composition containing a therapeutic amount of the Harderian secretion compound.

The present compositions can be solutions, although other forms, such as ointments, gels, creams, emulsions, and the like may be employed.

Accordingly, in some embodiments, the present invention provides methods of treating dry eye in a human in need thereof comprising opthalmically administering an effective amount of a compound found in Harderian gland secretions. In some embodiments, the compound is a lipid compound. In some embodiments, the lipid compound is an ether ester compound.

In some embodiments, the compound has the formula:

(I)

$$R^2 \underset{O}{\overset{O}{\|}} O \sim L^1 \sim O \sim R^1$$

wherein,
$R^1$ is an unsubstituted alkyl or alkenyl;
$R^2$ is an unsubstituted alkyl
$L^1$ is $-L^2-C(O)-L^3-$ or $-CH(-L^4-R^3)-L^3-$;
$L^2$ is a bond or an unsubstituted alkylene;
$L^3$ and $L^4$ are independently unsubstituted alkylene
$R^3$ is a hydroxyl or $-O-C(O)-R^4$ and
$R^4$ is unsubstituted alkyl.

In some embodiments, the compound has the formula:

(II)

$$R^2 \underset{O}{\overset{O}{\|}} O \sim \underset{R^3}{\overset{}{\mid}} \sim O \sim R^1 \quad \text{or}$$

(III)

$$R^2 \underset{O}{\overset{O}{\|}} O \sim \underset{O}{\overset{O}{\|}} O \sim R^1.$$

In some embodiments, the compound has the formula:

(IV)

$$R^2 \underset{O}{\overset{O}{\|}} O \sim \underset{O \sim R^1}{\overset{O \sim C(O) \sim R^4}{\mid}}$$

With respect to the structures above, in some embodiments, $R^1$ is unsubstituted $C_6$-$C_{30}$ alkyl or alkenyl; $R^2$ is unsubstituted $C_5$-$C_{31}$ alkyl; and $R^4$ is unsubstituted $C_5$-$C_{31}$ alkyl. In some embodiments, $R^1$ is unsubstituted $C_{14}$-$C_{22}$ alkyl or alkenyl; $R^2$ is unsubstituted $C_{13}$-$C_{17}$ alkyl; and $R^4$ is unsubstituted $C_{13}$-$C_{19}$ alkyl. In some embodiments, $R^2$ is an unsubstituted $C_{15}$ alkyl.

In some embodiments, the compound has the formula:

[chemical structures shown]

wherein: x, y and z are independently 5, 7, 9, 11, 13, 15, 17, 19, 21, 23, 25, 27 or 29; and
w is 8, 10, 12, 14, 16, 18, 20, 22, 24, 26, 28 or 30. In some embodiments, x is 11, 13, or 15;
y and z are independently 11, 13, 15 or 17; and w is 16, 18 or 20.

In some embodiments, the compound is selected from the group consisting of:

[chemical structures shown]

-continued

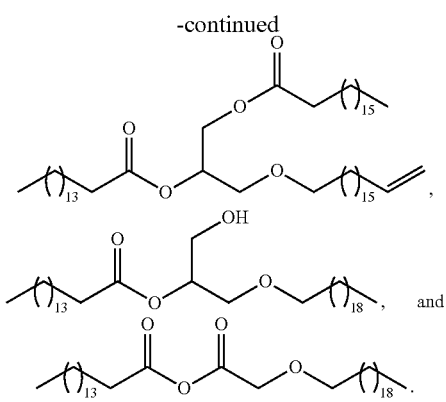

In some embodiments, the compound is administered in combination with a therapeutic agent. In some embodiments, the therapeutic agent is selected from the group consisting of: NMDA antagonists, antibacterials, antihistamines, decongestants, antiinflammatories, antiparasitics, miotics, sympathomimetics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, adrenergic anesthetics, beta blockers, alpha-2-agonists, cycloplegics, postaglandins, derivatives thereof and mixtures thereof.

In some embodiments, the Harderian gland is a rabbit Harderian gland. In some embodiments, the compound is administered topically.

In some embodiments, the compound is characterized by a mass spectrum (abscissa-mass-to-charge ratio m/z; ordinate-relative intensity) showing detected component ions from a Harderian gland secretion sample from the rabbit as shown in FIG. 1A. In some embodiments, the compound provides a mass chromatogram (abscissa-time in minutes; ordinate-Selected Ion Monitoring signal intensity) obtained from the HPLC liquid chromatography column separation of the Harderian secretion compounds at m/z 593, 791, 819, 847 as shown in FIG. 2 A, B, C, D. In some embodiments, the compound is characterized by a graph (abscissa-time in minutes; ordinate-signal intensity) showing TIC signals from the second MS analyzer m/z=593, 791, 819, 847 obtained for the HPLC/MS/MS Harderian secretion sample as shown in FIG. 3. In some embodiments, the Harderian gland lipid compound is characterized by HPLC/MS/MS mass spectra as shown in FIG. 4, wherein the parent ion and a plurality of fragment ions resulting from fragmentation of the parent ion making a combination for fragment ions selected from the group comprising: m/z 593, 377, 338, 319, 238; m/z 791, 551, 535, 317; m/z 819, 579, 563, 535, 479, 317; and m/z 847, 591, 563, 507, 317, 297. In some embodiments, the compound comprises parent ions having a particular m/z appearing in a mass spectrum and a function of mass units indicating a strong signal corresponding to molecular formula corresponding to the group comprising: C39H77O3, C51H99O5, C53H103O5, and C55H107O5 as shown in FIG. 5. In some embodiments, the compound has a chemical structures corresponding to one of the structures shown in FIG. 5.

In some embodiments, the present invention provides methods of treating dry eye in a human in need thereof comprising ophthalmically administering an effective amount of a compound having the formula:

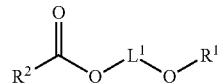

wherein, $R^1$ is an unsubstituted alkyl or alkenyl; $R^2$ is an unsubstituted alkyl; $L^1$ is $-L^2-C(O)-L^3-$ or $-CH(-L^4-R^3)-L^3-$; $L^2$ is a bond or an unsubstituted alkylene; $L^3$ and $L^4$ are independently unsubstituted alkylene; $R^3$ is a hydroxyl or $-O-C(O)-R^4$; and $R^4$ is unsubstituted alkyl. In some embodiments, the compound has the formula:

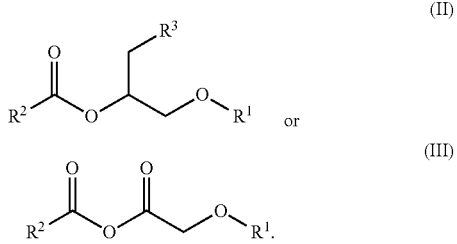

In some embodiments, the compound has the formula:

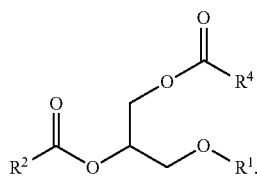

In some embodiments, $R^1$ is unsubstituted $C_6$-$C_{30}$ alkyl or alkenyl; $R^2$ is unsubstituted $C_5$-$C_{31}$ alkyl; and $R^4$ is unsubstituted $C_5$-$C_{31}$ alkyl. In some embodiments, $R^1$ is unsubstituted $C_{14}$-$C_{22}$ alkyl or alkenyl; $R^2$ is unsubstituted $C_{13}$-$C_{17}$ alkyl; and $R^4$ is unsubstituted $C_{13}$-$C_{19}$ alkyl. In some embodiments, $R^2$ is an unsubstituted $C_{15}$ alkyl. In some embodiments, the compound has the formula:

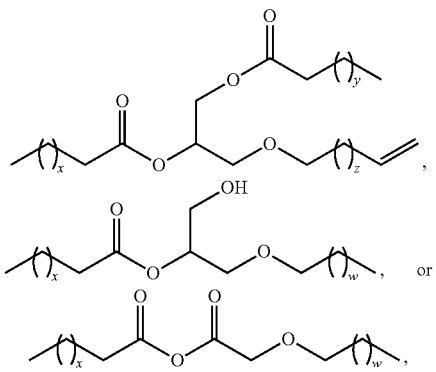

wherein:
x, y and z are independently 5, 7, 9, 11, 13, 15, 17, 19, 21, 23, 25, 27 or 29; and w is 8, 10, 12, 14, 16, 18, 20, 22, 24, 26, 28 or 30. In some embodiments, x is 11, 13, or 15;
y and z are independently 11, 13, 15 or 17; and w is 16, 18 or 20. In some embodiments, the compound is selected from the group consisting of:

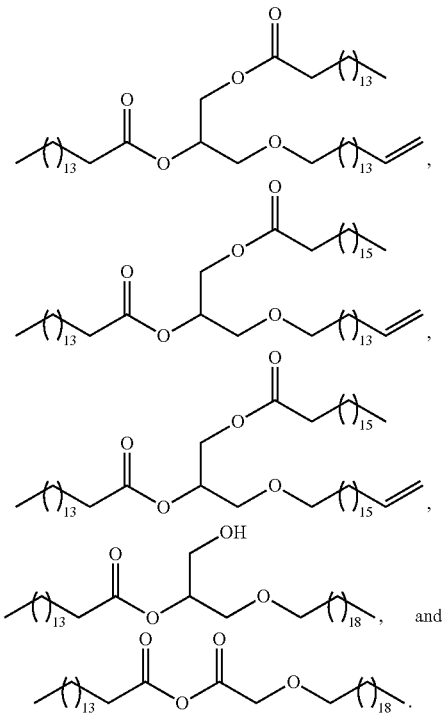

and

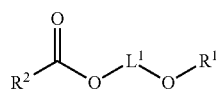

In some embodiments, the present invention provides a pharmaceutical composition comprising a compound having the formula:

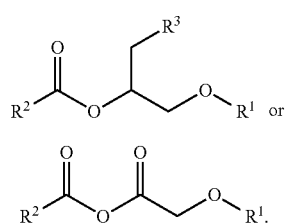
(I)

wherein, $R^1$ is an unsubstituted alkyl or alkenyl; $R^2$ is an unsubstituted alkyl;
$L^1$ is -$L^2$-C(O)-$L^3$- or —CH(-$L^4$-$R^3$)-$L^3$-; $L^2$ is a bond or an unsubstituted alkylene;
$L^3$ and $L^4$ are independently unsubstituted alkylene; $R^3$ is a hydroxyl or —O—C(O)—$R^4$; and
$R^4$ is unsubstituted alkyl. In some embodiments, the compound has the formula:

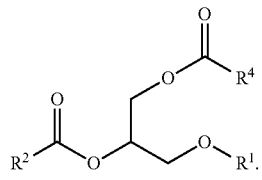
(IV)

In some embodiments, $R^1$ is unsubstituted $C_6$-$C_{30}$ alkyl or alkenyl; $R^2$ is unsubstituted $C_5$-$C_{31}$ alkyl; and $R^4$ is unsubstituted $C_5$-$C_{31}$ alkyl. In some embodiments, $R^1$ is unsubstituted $C_{14}$-$C_{22}$ alkyl or alkenyl; $R^2$ is unsubstituted $C_{13}$-$C_{17}$ alkyl; and $R^4$ is unsubstituted $C_{13}$-$C_{19}$ alkyl. In some embodiments, $R^2$ is an unsubstituted $C_{15}$ alkyl. In some embodiments, the compound has the formula:

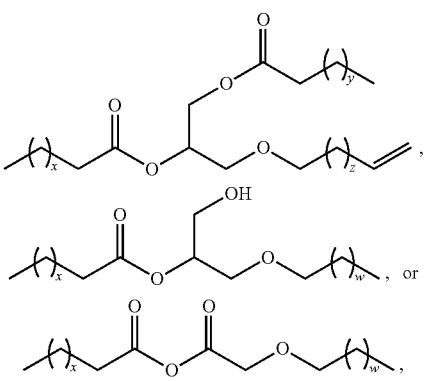

wherein:

x, y and z are independently 5, 7, 9, 11, 13, 15, 17, 19, 21, 23, 25, 27 or 29; and w is 8, 10, 12, 14, 16, 18, 20, 22, 24, 26, 28 or 30. In some embodiments, x is 11, 13, or 15;

y and z are independently 11, 13, 15 or 17; and w is 16, 18 or 20. In some embodiments, the composition is selected from the group consisting of:

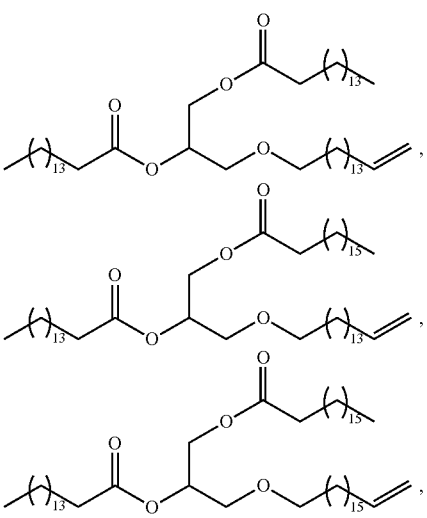

In some embodiments, the compound has the formula:

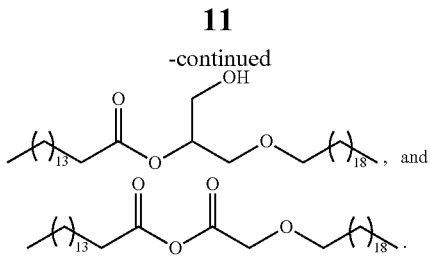

In some embodiments, the present invention provides a pharmaceutical composition for treating dry eye in a human in need thereof comprising an effective amount of a Harderian lipid compound obtained from Harderian gland secretions combined with a therapeutic agent. In some embodiments, the therapeutic agent is selected from the group consisting of therapeutic component comprises a material selected from the group consisting of NMDA antagonists, antibacterials, antihistamines, decongestants, antiinflammatories, antiparasitics, miotics, sympathomimetics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, adrenergic anesthetics, beta blockers, alpha-2-agonists, cycloplegics, postaglandins, derivatives thereof and mixtures thereof.

In some embodiments, the present invention provides a lipid compound in its essentially pure form having the following characteristics;
(a) mass spectra (abscissa-mass-to-charge ratio m/z; ordinate-relative intensity) showing detected component ions from a Harderian secretion sample from the rabbit (FIG. 1A)
(b) mass chromatogram (abscissa-time in minutes; ordinate-Selected Ion Monitoring signal intensity) obtained from the HPLC liquid chromatography column separation of the Harderian secretion compounds at m/z 593, 791, 819, 847 as shown in FIG. 2A, B, C, D.
(c) a graph (abscissa-time in minutes; ordinate-signal intensity) showing TIC signals from the second MS analyzer m/z=593, 791, 819, 847 obtained for the HPLC/MS/MS Harderian secretion sample as shown in FIG. 3.
(d) HPLC/MS/MS mass spectra as shown in FIG. 4, wherein the parent ion and a plurality of fragment ions resulting from fragmentation of the parent ion making a combination for fragment ions selected from the group comprising:
m/z 593, 377, 338, 319, 238
m/z 791, 551, 535, 317
m/z 819, 579, 563, 535, 479, 317; and
m/z 847, 591, 563, 507, 317, 297.
(e) parent ions having a particular m/z appearing in a mass spectrum and a function of mass units result in indicating a strong signal corresponding to molecular formula corresponding to the group comprising: C39H77O3, C51H99O5, C53H103O5, and C55H107O5 as shown in FIG. 5.
(f) A chemical structure corresponding to at least one of the structures shown in FIG. 5.

In some embodiments, the present invention provides a lipid compound in its essentially pure form having the formula:

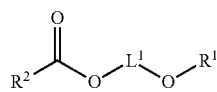

(I)

wherein,
$R^1$ is an unsubstituted alkyl or alkenyl;
$R^2$ is an unsubstituted alkyl;
$L^1$ is -$L^2$-C(O)-$L^3$- or —CH(-$L^4$-$R^3$)-$L^3$-;
$L^2$ is a bond or an unsubstituted alkylene;
$L^3$ and $L^4$ are independently unsubstituted alkylene
$R^3$ is a hydroxyl or —O—C(O)—$R^4$; and
$R^4$ is unsubstituted alkyl.

In some embodiments, the lipid compound has the formula:

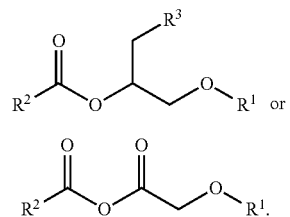

In some embodiments, the lipid compound has the formula:

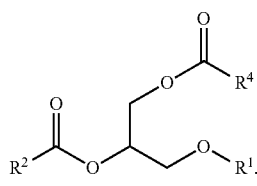

In some embodiments, $R^1$ is unsubstituted $C_6$-$C_{30}$ alkyl or alkenyl; $R^2$ is unsubstituted $C_5$-$C_{31}$ alkyl; and $R^4$ is unsubstituted $C_5$-$C_{31}$ alkyl. In some embodiments, $R^1$ is unsubstituted $C_{14}$-$C_{22}$ alkyl or alkenyl; $R^2$ is unsubstituted $C_{13}$-$C_{17}$ alkyl; and $R^4$ is unsubstituted $C_{13}$-$C_{19}$ alkyl. In some embodiments, $R^2$ is an unsubstituted $C_{15}$ alkyl. In some embodiments, the lipid compound has the formula:

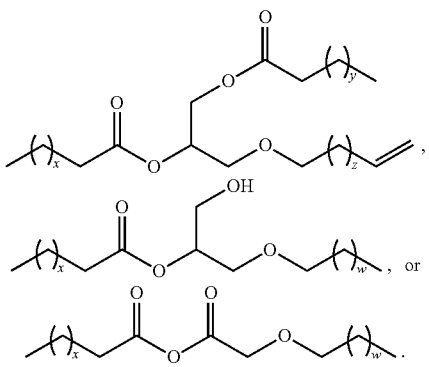

Wherein x, y and z are independently 5, 7, 9, 11, 13, 15, 17, 19, 21, 23, 25, 27 or 29; and
w is 8, 10, 12, 14, 16, 18, 20, 22, 24, 26, 28 or 30. In some embodiments, x is 11, 13, or 15;
y and z are independently 11, 13, 15 or 17; and w is 16, 18 or 20. In some embodiments, the lipid compound formula is selected from the group consisting of:

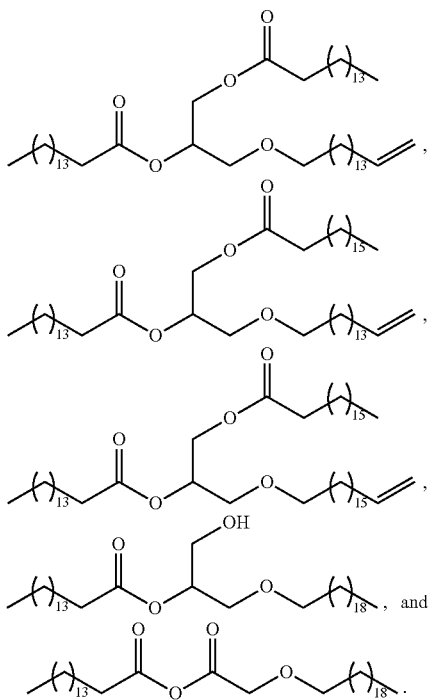

In some embodiments, the present invention provides, an ophthalmic vehicle comprising a Harderian lipid compound. In some embodiments, the Harderian lipid compound is an ether ester compound. In some embodiments, the ether ester compound is a dietherester compound. In some embodiments, the Harderian lipid compound has the formula:

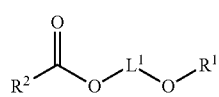

(I)

wherein, $R^1$ is an unsubstituted alkyl or alkenyl; $R^2$ is an unsubstituted alkyl;

$L^1$ is $-L^2-C(O)-L^3-$ or $-CH(-L^4-R^3)-L^3-$; $L^2$ is a bond or an unsubstituted alkylene;

$L^3$ and $L^4$ are independently unsubstituted alkylene; $R^3$ is a hydroxyl or $-O-C(O)-R^4$; and $R^4$ is unsubstituted alkyl. In some embodiments, the Harderian lipid compound has the formula:

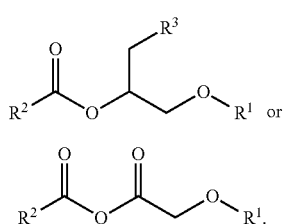

In some embodiments, the Harderian lipid compound has the formula:

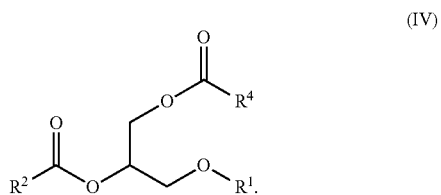

In some embodiments, $R^1$ is unsubstituted $C_6-C_{30}$ alkyl or alkenyl; $R^2$ is unsubstituted $C_5-C_{31}$ alkyl; and $R^4$ is unsubstituted $C_5-C_{31}$ alkyl. In some embodiments, $R^1$ is unsubstituted $C_{14}-C_{22}$ alkyl or alkenyl; $R^2$ is unsubstituted $C_{13}-C_{17}$ alkyl; and $R^4$ is unsubstituted $C_{13}-C_{19}$ alkyl. In some embodiments, $R^2$ is an unsubstituted $C_{15}$ alkyl. In some embodiments, the compound further comprises:

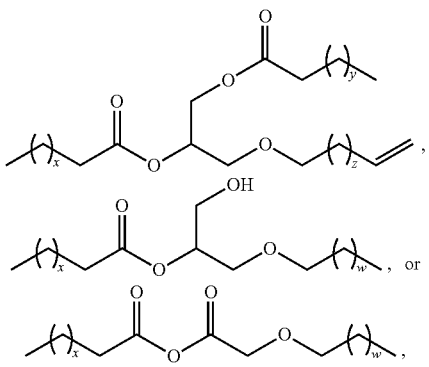

wherein x, y and z are independently 5, 7, 9, 11, 13, 15, 17, 19, 21, 23, 25, 27 or 29; and w is 8, 10, 12, 14, 16, 18, 20, 22, 24, 26, 28 or 30. In some embodiments, x is 11, 13, or 15;

y and z are independently 11, 13, 15 or 17; and w is 16, 18 or 20.

In some embodiments, the compound has the formula:

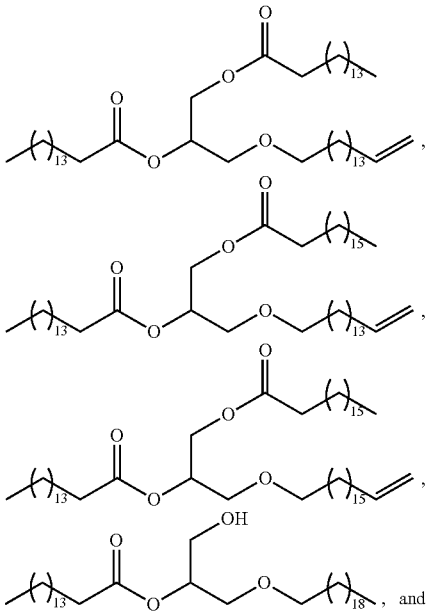

-continued

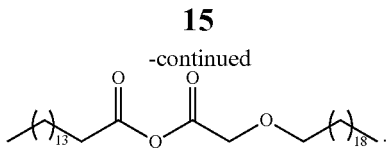

In some embodiments, the combination of the Harderian compound and the therapeutic agent is more effective when administered to the eye to relieve symptoms of dry eye relative to an identical composition without the Harderian lipid compound.

In some embodiments, the methods for treating dry eye in a human in need thereof comprise opthalmically administering an effective amount of lipid composition improving dry eye of a human in need of such improvement, thereby providing at least one additional benefit to the eye.

BRIEF DESCRIPTION OF THE DRAWING FIGURES

FIGS. 1 A & B illustrate ESI mass spectra (abscissa-mass-to-charge ratio m/z; ordinate-relative intensity) showing detected component parent, fragment, and quasi-molecular ions [M+H]$^+$, of a Harderian secretion sample from the rabbit (FIG. 1A) and from a human tear sample (FIG. 1B).

FIGS. 2 A, B, C, D illustrate a HPLC/MS chromatogram (abscissa-time in minutes; ordinate-Selected Ion Monitoring signal intensity) obtained from the HPLC liquid chromatography column separation of the Harderian secretion compounds at m/z=593, 791, 819, 847.

DETAILED DESCRIPTION

Definitions

Figure 1A:
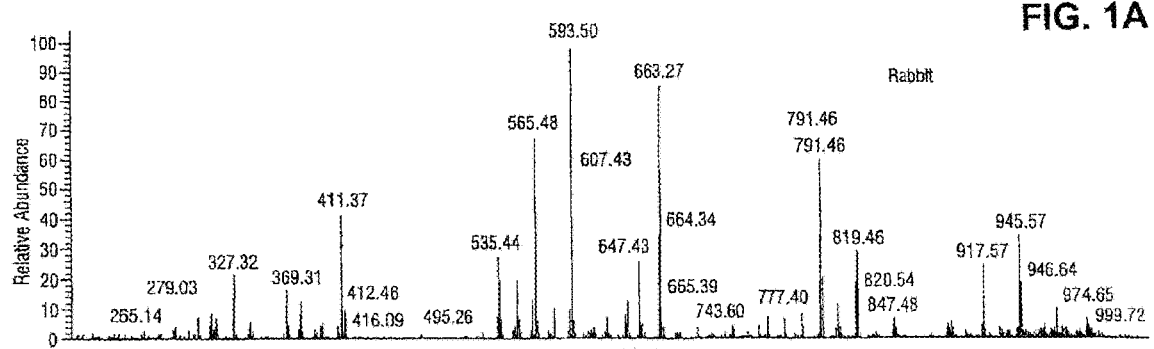

"Alkyl" refers to a monovalent straight-chain, branched or cyclic saturated aliphatic hydrocarbon radical. Preferably, the alkyl group is a straight chain radical having 1 to 40 carbon atoms. More preferably, it is an alkyl radical of from 5 to 31 carbon atoms, most preferably 13 to 17 carbon atoms. Typical alkyl radicals include pentyl, hexyl, tridecanyl, tetradecanyl, nonadecanyl, docosanyl, triacontanyl, hentriacontanyl and the like. Preferably this term denotes an acyclic carbon or a saturated acyclic carbon chain represented by the formula CnH2n+1 wherein n is an integer of from 1 to 31.

"Alkenyl" refers to a monovalent, straight-chain, branched or cyclic, unsaturated aliphatic hydrocarbon radical having one or more, preferably one, double bond. Preferably, the alkenyl radical has from 2 to 40 carbon atoms. More preferably, it is an alkenyl radical of from 6 to 30 carbon atoms, most preferably 14 to 22 carbon atoms. Typical alkenyl groups include hexenyl, tridecenyl, tetradecenyl, nonadecenyl, docosenyl, triacontenyl, hentriacontenyl and the like. Preferably this term denotes an acyclic carbon chain which contains a carbon-to-carbon double bond and is represented by the formula CnH2n−1 wherein n is an integer of from 2 to 40.

"Alkylene" refers to a divalent, straight-chain, branched or cyclic, saturated aliphatic hydrocarbon radical. Preferably, the alkylene group has from 1 to 12 carbon atoms. This term denotes an acyclic carbon or a saturated acyclic carbon chain represented by the formula CnH2n−2 wherein n is an integer of from 1 to 12. More preferably, it is a lower alkylene of from 1 to 7 carbon atoms, most preferably from 1 to 4 carbon atoms, e.g., methylene.

As used herein, the term "lipid" refers to water-insoluble organic substances naturally found in cells that are extractable by nonpolar solvents such as chloroform, ether, or benzene. Lipids generally serve four general functions: (1) as structural components of membranes; (2) as intracellular storage depots of metabolic fuel; (3) as a transport form of metabolic fuel; and (4) as protective components of cell walls of many organisms. Some examples of natural lipids are long-chain fatty acids, fatty acid esters, acylglycerols, phosphoglycerides, steroids, waxes, terpenes, and fat-soluble vitamins As used herein, the term "mass-to-charge ratio" refers to the ratio of the mass of a detected fragment in a mass spectrometer over the charge of that same detected fragment. The mass-to-charge ratio is abbreviated as m/z.

As used herein, the term MS refers to "mass spectrometry" and related variations on the word "spectrometry" where one of skill in the art will appreciate the words are also appropriate.

As used herein, the term MW refers to "molecular weight" and related variations of atomic mass units used in mass spectrometry where one of skill in the art will appreciate the other units are al so appropriate.

As used herein, the term chemical formula includes information about the spatial arrangement of bonds in a chemical but not necessarily the exact isomer; while the term molecular formula refers to the number of atoms of each element in the compound.

As used herein, the term "analytical technique" refers to a method for deterring a property of a particular substance. Preferred analytical techniques include those having an ionizing source, such as for example, mass spectrometry. One of skill in the art will appreciate that other analytical techniques can be used in the instant invention.

Liquid chromatography is commonly used as a means of physically separating compounds in a mixture and is used to purify, quantify, and identify individual components of the mixture. High pressure liquid chromatography (HPLC), approximately 40 MPa, utilizes a stationary phase of particles, approximately 2-5 um in diameter, densely packed in a 1-2 mm separatory column, a pump that moves the mobile phase and compound through the stationary phase, and a detector that provides a characteristic retention time for the eluted compounds. The detector may also provide characteristic data for each compound such as an ultraviolet-visible spectrum, fluorescence detection, or data from a mass spectrometer. The retention time of the compounds in the mixture depends on the strength of the interaction with the stationary phase.

Normal phase HPLC refers to a method or separating compounds based on adsorption to a stationary surface and by polarity: the most nonpolar compounds elude first and the most polar compounds elute last. The normal stationary phase is polar, while a non-polar, non-aqueous mobile phase work to separating compounds in non-polar solvents. The use of more polar solvents or gradient elution mixtures of solvents, such as miscible combinations of water, methanol and acetonitrile, in the mobile phase decreases the retention time of the compounds where use of more hydrophobic solvents increases retention times.

The eluent from the liquid chromatography column can then be detected and the separated components can be mass analyzed. The analysis can be performed online, by feeding the liquid eluting from the LC column directly to an electrospray, or offline, by collecting fractions to be later analyzed in an electrospray-mass spectrometry setup.

Electrospray is a gentle technique for ionizing molecules and leads to (quasi-) molecular ions. Electrospray ionization (ESI) is a technique used in mass spectrometry to produce ions. It is especially useful in producing ions from macromolecules because it overcomes the propensity of these molecules to fragment when ionized.

The ions observed by ESI mass spectrometry may be quasimolecular ions created by the addition of a proton (a hydrogen ion) and denoted $[M+H]^+$, or of another cation such as sodium ion, $[M+Na]^+$, or the removal of a proton, $[M-H]^-$. Multiply-charged ions such as $[M+nH]^{n+}$, wherein n is an integer, are often observed. For large macromolecules, there can be many charge states, resulting in a characteristic charge state envelope. All these are even-electron ion species: electrons (alone) are not added or removed, unlike in some other ionization sources. The analytes are sometimes involved in electrochemical processes, leading to shifts of the corresponding peaks in the mass spectrum.

As used herein, the term "total ion chromatogram or TIC" refers to the graph (abscissa-time in minutes; ordinate-ion signal intensity) showing a total ion signal or full scan obtained for the sample by a mass spectrometer detector. As used herein, the term "scanning or single ion monitoring" spectrometer refers to ions of the selected mass-to-charge ratio m/z to pass to the output port of the mass filter. Select scanning or single ion monitoring may be used to select ions of particular m/z, or a range of m/z ions, forming a plurality of ions generated by the source and is used to located particular ions within that m/z range specified or to select single ion m/z in what is referred to as select or single ion monitoring (SIM). Typically the ion detector collects the ions and converts them to a signal to measure the intensity of the ions as a computer display, typically as a graph (abscissa-time in minutes; ordinate-signal intensity) showing a signal specified. One of skill in the art will appreciate that other analytical techniques can be used in the instant invention.

As used herein, the term "high-pressure liquid chromatography tandem mass spectrometry" refers to a mass spectrometry technique that is known to one of skill in the art and involves obtaining a sample from a high-pressure liquid chromatograph system utilized to separate compounds from compound mixtures and deliver a liquid sample to a mass spectrometer sample inlet. The sample is ionized in the mass spectrometer coupling two stages of mass analysis so as to subject a particular fragment of a first ionization process to a subsequent ionization process. Tandem mass spectrometers operate by using the separation of ions as a first fractionation step. Before entering the second mass spectrometer, ion fractions from the first MS analyzer are fragmented, usually by passage through a neutral collision gas to induce fragmentation, to a second MS analyzer. These fragment ions exist as a subset of the original parent ions. Analysis of m/z spectrum of these subset ions are used to determine fragmentation patterns without interference from other ion fractions. The device handling system is operably connected to the mass spectrometer under the direction of computer control. One skilled in the art will appreciate that other analytical techniques can be used in the instant invention.

The Harderian lipid compound may be represented as:

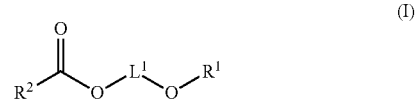

(I)

wherein,
$R^1$ is an unsubstituted alkyl or alkenyl;
$R^2$ is an unsubstituted alkyl
$L^1$ is $-L^2-C(O)-L^3-$ or $—CH(-L^4-R^3)-L^3-$;
$L^2$ is a bond or an unsubstituted alkylene;
$L^3$ and $L^4$ are independently unsubstituted alkylene;
$R^3$ is a hydroxyl or $—O—C(O)—R^4$; and
$R^4$ is unsubstituted alkyl.

The Harderian lipid compounds of Formula I are related by a basic chemical structure represented by:

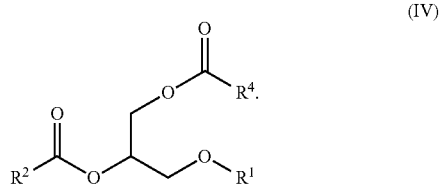

(IV)

where $R^1$ is unsubstituted $C_6$-$C_{30}$ alkyl or alkenyl; $R^2$ is unsubstituted $C_5$-$C_{31}$ alkyl; and $R^4$ is unsubstituted $C_5$-$C_{31}$ alkyl. Alternatively, $R^1$ is unsubstituted $C_{14}$-$C_{22}$ alkyl or alkenyl; $R^2$ is unsubstituted $C_{13}$-$C_{17}$ alkyl; and $R^4$ is unsubstituted $C_{13}$-$C_{19}$ alkyl. More preferably, $R^2$ is an unsubstituted $C_{15}$ alkyl.

The preferred compounds of formula IV are

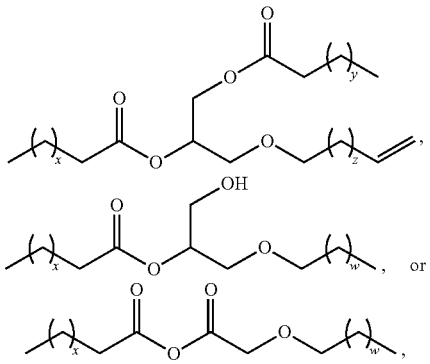

wherein the alkyl units are as follows:
x, y and z are independently 5, 7, 9, 11, 13, 15, 17, 19, 21, 23, 25, 27 or 29; and w is 8, 10, 12, 14, 16, 18, 20, 22, 24, 26, 28 or 30 and
alternatively, wherein x is 11, 13, or 15; y and z are independently 11, 13, 15 or 17; and w is 16, 18 or 20.

As used herein, these compounds are related by a basic chemical structure represented by

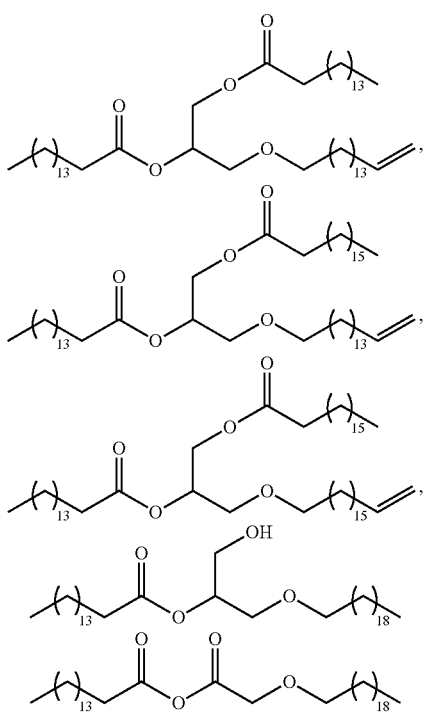

The above compounds may be isolated from Harderian gland secretions or synthesized by methods known in the art, e.g., by solvent extraction of a lipid component from the secretions of the Harderian gland followed, if desired by chromatographic separation of the individual compounds comprising said solvent-extracted lipid component.

The Harderian lipid compounds may be administered to a patient needing treatment for dry eye in combination with a opthalmically-acceptable vehicle or carrier. Other components, which may be included in the carrier components include, without limitation, buffer components, tonicity components, preservative-components, pH adjustors, components commonly found in artificial tears, such as one or more electrolytes, and the like and mixtures thereof. In one very useful embodiment the carrier component includes at least one of the following: an effective amount of a buffer component; an effective amount of a tonicity component; an effective amount of is a preservative component; and water.

These additional components preferably are ophthalmically acceptable and can be chosen from materials which are conventionally employed in ophthalmic compositions, for example, compositions used to treat eyes afflicted with dry eye syndrome, artificial tear formulations and the like.

Acceptable effective concentrations for these additional components in the compositions of the invention are readily apparent to the skilled practitioner.

Said compounds may be administered, alone, or in combination with pharmaceutically acceptable substances including buffer solutions, for example phosphate buffered saline, or inert carrier compounds, glycerols, mineral oils or similar substances to the ocular surface of the eye.

The dosage of the above lipid compounds is optimized according to the formulation and method of delivery and the mode of administration is determined by conventional protocols and effectively treats "dry eye" symptoms in humans.

Said Harderian lipid compound may be utilized as a vehicle for topical administration of a therapeutic medicament. In particular, said Harderian lipid compound-containing vehicle is used to deliver any desired therapeutic agent, or combination of therapeutic agents, including an antibiotic agent, an antiviral agent, an antifungal agent, an anti-cancer agent, an antiglaucoma agent, an antiinflammatory agent, an analgesic, an immunomodulatory agent, a macro-molecule, or a mixture thereof.

Therapeutic agents that are used in the method of the present invention include, but are not limited to NMDA antagonists, antihistamines, antiparasitics, miotics, sympathomimetics, anticholinergics, local anesthetics, amoebicidals, trichomonocidals, mydriatics, carbonic anhydrase inhibitors, ophthalmic diagnostic agents, ophthalmic agents used as adjuvants in surgery, chelating agents, antineoplastics, diagnostics, adrenergic anesthetics, beta blockers, alpha-2-agonists, cycloplegics, prostaglandins, ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciprofloxacin, etc.; sulfonamides such as chloramine T; and sulfones such as sulfanilic acid as the hydrophilic entity, anti-viral drugs, e.g. acyclovir, gancyclovir, vidarabine, azidothymidine, dideoxyinosine, dideoxycytosine, dexamethasone, ciprofloxacin, water soluble antibiotics, such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, ketorolac, naproxen, etc., an anesthetic, e.g. lidocaine; .beta.-adrenergic blocker or .beta.-adrenergic agonist, e.g. ephidrine, epinephrine, etc.;

aldose reductase inhibitor, e.g. epalrestat, ponalrestat, sorbinil, tolrestat; antiallergic, e.g. cromolyn, beclomethasone, dexamethasone, and flunisolide; colchicine; antiamebic agents, e.g. chloroquine and chlortetracycline; and antifungal agents, e.g. amphotericin, etc., anti-angiogenesis compounds such as anecortave acetate, anti-glaucoma agents, such as brimonidine, acetozolamide, bimatoprost, Timolol, mebefunolol; memantine; alpha-2 adrenergic receptor agonists; 2ME2; anti-neoplastics, such as vinblastine, vincristine, interferons; alpha., beta. and .gamma., antimetabolites, such as folic acid analogs, purine analogs, and pyrimidine analogs; immunosuppressants such as azathiprine, cyclosporine and mizoribine; miotic agents, such as carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like, including derivatives thereof and mixtures thereof.

These and other aspects, objects, and embodiments will be more apparent in the accompanying specific examples and drawing figures.

Example 1

Harderian lipids tear secretions are collected from living rabbits and extracts are made from rabbit Harderian glands.

Control tear secretions are collected from normal human subjects as opposed to human subjects that are suffering from dry eye. These samples were analyzed by ESI-CI/MS/MS and are represented as the Harderian sample in FIG. 1A and the human tear sample in FIG. 1B. Comparing the mass spectra of FIG. 1A and FIG. 1B, the Harderian compound at m/z=593, and the plurality of related compounds, are not found in the human spectral sample.

Figure 3:
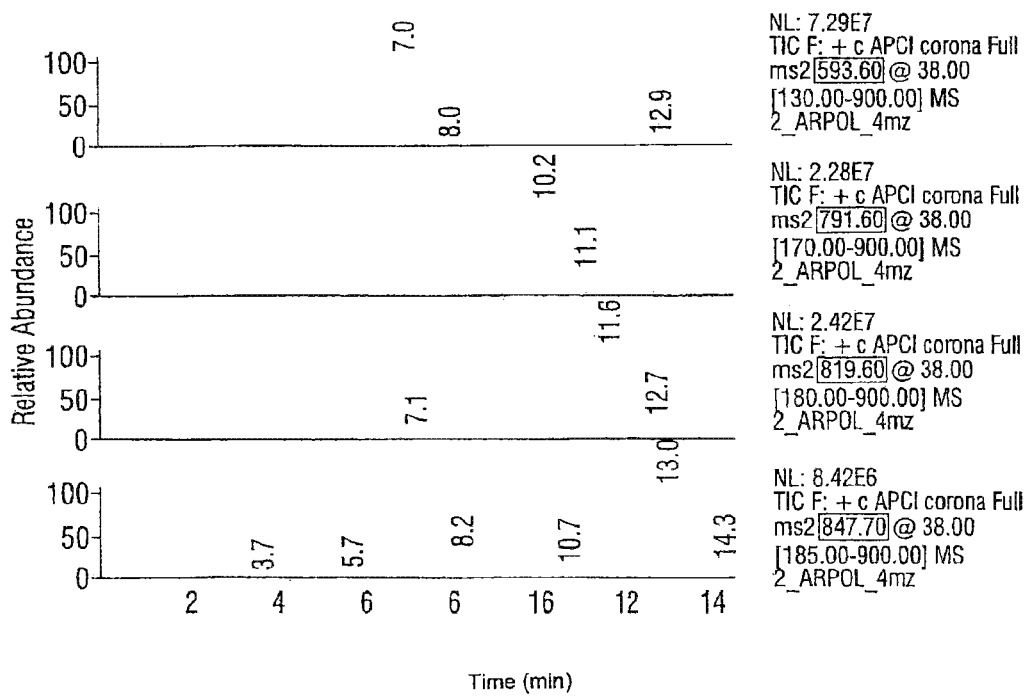
FIG. 3 is a graph (abscissa-time in minutes; ordinate-signal intensity) showing TIC signals from the second MS analyzer m/z=593, 791, 819, 847 obtained for the HPLC/MS/MS Harderian secretion sample. The data here are complimentary to the data of FIG. 2.
Figure 4:
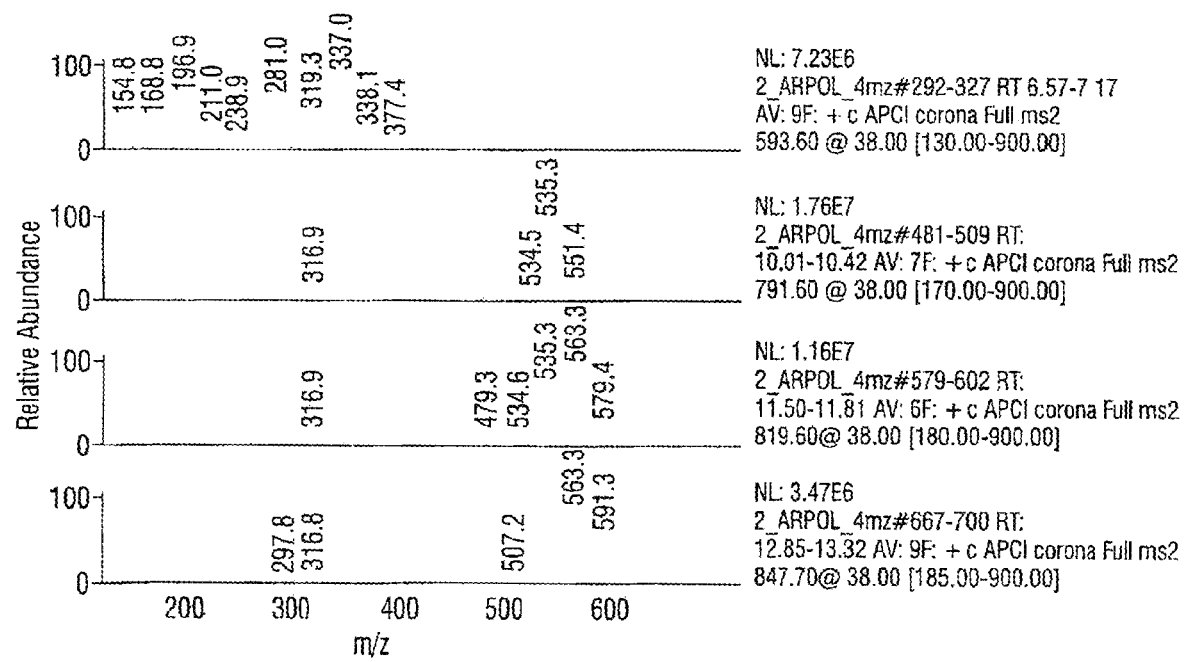
FIG. 4 shows ESI/APICI MS/MS mass spectral fragmentation traces (abscissa-mass-to-charge ratio m/z; ordinate-relative intensity) for Harderian secretion compounds at m/z=593, 791, 819, 847.
Figure 5:
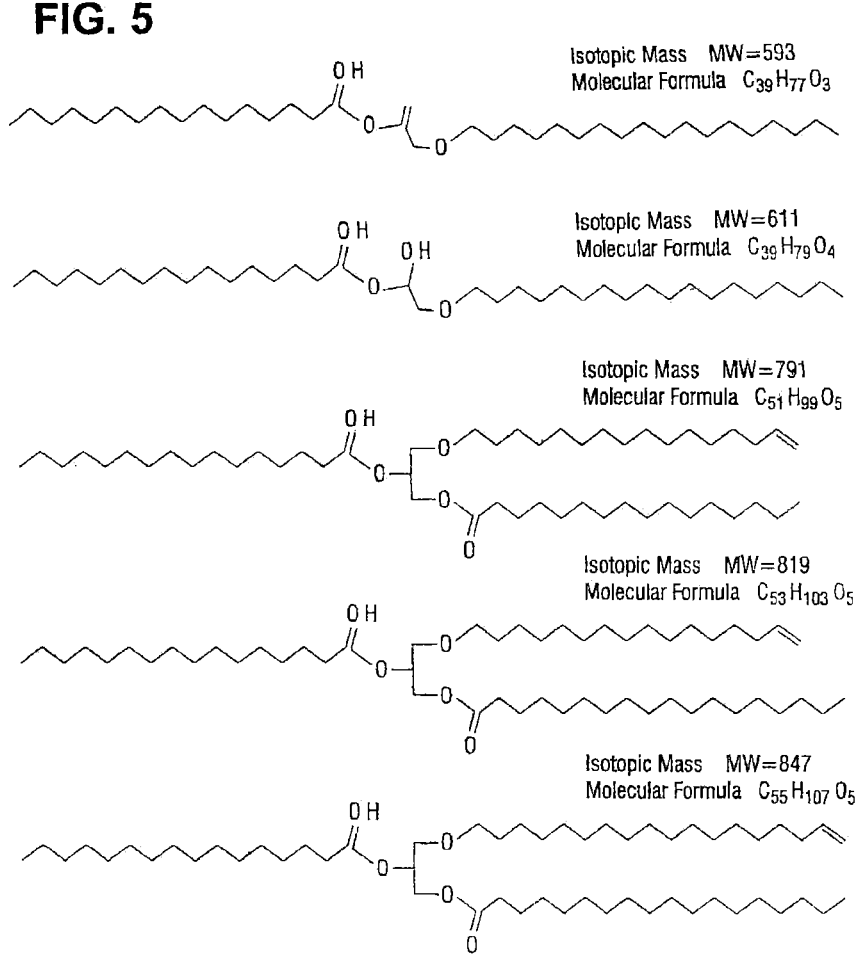
FIG. 5 shows characterization data including molecular weight and structural identification for five Harderian secretion compounds.

The lipids are initially separated from the Haderian gland secretions of rabbits by normal phase HPLC separation followed immediately by mass spectrometry using chemical ionization of the separated lipid (HPLC/ESI-CI/MS/MS) as shown in FIG. 2. Four compounds identified by this process are unique to rabbits and are thought to have their origins in the Harderian gland and their spectral patterns are further isolated by MS/MS techniques as shown in FIGS. 3-4. The mass fragmentation patterns of the separated lipids indicate they are structurally related to each other and to chemical structure m/z=593.

In the case of the compound at m/z=593, a standard based on the theoretical structure is synthesized, and the fragmentation pattern of the standard confirms the theoretical structure of the isolated lipid it was based upon.

Quasi molecular ions are inferred with use of ESI/API-CI/MS/MS techniques with an addition of a proton (a hydrogen ion) and denoted $[M+H]^+$, or the removal of a proton, $[M-H]^-$. Multiply-charged ions such as $[M+nH]^{n+}$ are often observed. This leads to shifts of the corresponding peaks in the mass spectrum. Therefore, the ions from the Harderian rabbit gland secretions may have molecular weights within a range of atomic mass units which includes a hydrogen ion. The depiction of this variable is taken into account during the analytical scans as shown in FIGS. 2-4.

The mass spectrometric analysis of the rabbit Harderian gland secretions are characterized by HPLC/MS/MS mass spectrometry wherein the parent ion and a plurality of fragment ions, quasi molecular ions, molecular weights, and molecular formula are identified as follows:

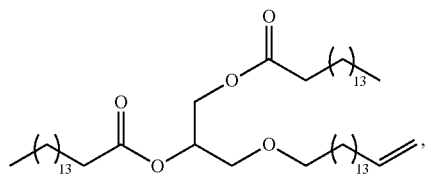

m/z=791, 551, 535, 317
MW $[M+H]^+$=791
molecular formula=C51H99O5
retention time 22.2 min

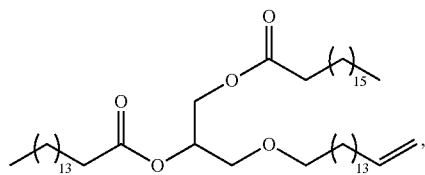

m/z=819, 579, 563, 535, 479, 317
MW $[M+H]^+$=891
molecular formula=C53H103O5
HPLCMS retention time=23.8 min

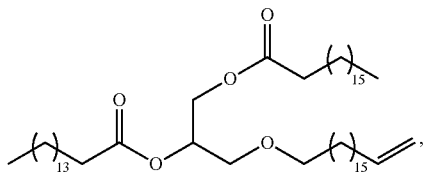

m/z=847, 591, 563, 507, 317, 297
MW $[M+H]^+$=847
molecular formula=C55H107O5
HPLCMS retention time=25.4 min

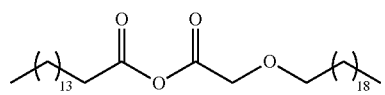

m/z=593, 377, 338, 319, 238
MW $[M+H]^+$=593
molecular formula=C39H77O3
HPLC retention times=6.9, 16.7, 22.2, 23.8 min

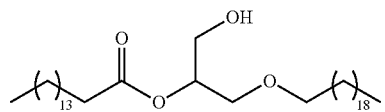

MW=611
molecular formula=C39H79O4
hydrolyzed form of MW=593

Mass spectra of the above lipid compounds may also appear in hydrolyzed, dehydrolyzed, and/or rearrangements of unsaturated functional groups. For example, the unstable Harderian compound at m/z=611 may alternatively be represented as chemically ionized or in its dehydrated form as MW=593, for example, R1 is a C20 alkyl group and R2 is a C13 alkyl group. It is also possible the compound at m/z=593 has several chemically structurally related forms with alternative functional groups as it has four HPLC retention times and coelutes with two of the other Harderian compounds.

Example 2

The Harderian gland secretion or tears from a rabbit containing identified HPLC/MS/MS compound m/z=593 is ophthalmically administered in an effective amount to treat "dry eye" of a human. The quantified amount of the compound m/z=593 is comparable to the quantified amount of lipid in the human tear sample represented by FIG. 1B. The effective amount of the compound is specified by routine methods and is administered in combination with pharmaceutically acceptable substances including buffer solutions, for example phosphate buffered saline, or inert carrier compounds, glycerols, mineral oils or similar substances to the ocular surface of the eye. The dosage of rabbit Harderian gland secretion including the compound m/z=593 is optimized according to the formulation and method of delivery and the mode of administration is determined by conventional protocols and effectively treats "dry eye" symptoms in humans.

Figure 1B:
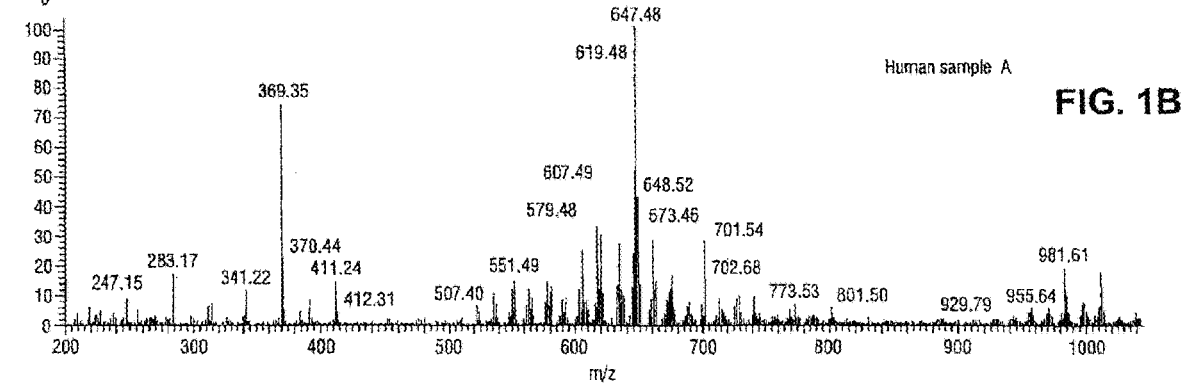

A second pharmaceutical composition comprising the Harderian gland secretion or tears from a rabbit containing identified HPLC/MS/MS compounds, including the compound m/z=593, is ophthalmically administered in an effective amount to treat "dry eye" of a human. The quantified amount of the compounds identified in FIG. 1A is comparable to the quantified amount of lipid in the human tear sample represented by FIG. 1B. The effective amount of the compound is specified by routine methods and is administered in combination with pharmaceutically acceptable substances including buffer solutions, for example phosphate buffered saline, or inert carrier compounds, glycerols, mineral oils or similar substances to the ocular surface of the eye. The dosage of rabbit Harderian gland secretion including the identified compounds including compound m/z=593 is optimized according to the formulation and method of delivery and the mode of administration is determined by conventional protocols and effectively treats "dry eye" symptoms in humans.

The results of testing the effect of the identified representative Harderian lipid compounds indicate all are effective in treating "dry eye" conditions of humans, although to various degrees.

Example 3

A new composition related to the Harderian gland secretions is synthesized based on the theoretical structure and the fragmentation pattern of the standard confirms the theoretical structure of the isolated lipid m/z=593 upon which it is based.

The effective amount of the synthesized compound administered is specified by routine methods and is administered, in combination with pharmaceutically acceptable substances including buffer solutions, for example phosphate buffered saline, or inert carrier compounds, glycerols, mineral oils or similar substances, to the ocular surface of the eye. The dosage of rabbit Harderian gland secretion including the synthesized compound is optimized according to the formulation and method of delivery and the mode of administration is determined by conventional protocols and effectively treats "dry eye" symptoms in humans.

A second composition related to the Harderian gland secretions is synthesized including the plurality of lipid compounds in Example 1. The effective amount of the plurality of lipid compounds administered is specified by routine methods and is administered, in combination with pharmaceutically acceptable substances including buffer solutions, for example phosphate buffered saline, or inert carrier compounds, glycerols, mineral oils or similar substances, to the ocular surface of the eye. The dosage of said second composition is optimized according to the formulation and method of delivery and the mode of administration is determined by conventional protocols and effectively treats "dry eye" symptoms in humans.

The results of testing the effect of the synthetic representative Harderian compounds indicate all are effective in treating "dry eye" conditions of humans, although to various degrees.

Example 4

The present invention further includes an ophthalmic vehicle comprising one or more of said Harderian lipid compounds. The vehicle comprises quantified amounts of the compound containing m/z=593 and the compounds related to m/z=791, 819, 847 (FIG. 1A), either as obtained from Handerian gland secretions or synthesized, and may be comparable to the quantified amount of lipid in the human tear sample represented by FIG. 1B to treat "dry eye" symptoms of a human.

The effective amount of said Harderian lipid compounds administered as a vehicle is specified by routine methods and may be combined with pharmaceutically acceptable substances utilized in ophthalmic vehicles, including buffer solutions, for example phosphate buffered saline, or inert carrier compounds, glycerols, mineral oils or similar substances. The dosage of said Harderian lipid compound is optimized according to the formulation and method of delivery and the mode of administration are determined by conventional protocols to effectively treat "dry eye" symptoms in humans.

Said Harderian lipid compound-containing vehicle is administered topically, e.g. as an eye drop, to provide "artificial tears."

Said Harderian lipid compound-containing vehicle is used in a method of treating a patient suffering from "dry eye" and related ocular disorders to provide improved stability of the tear film of a patient in need of said treatment.

Said Harderian lipid compound may be utilized as a vehicle for topical administration of a therapeutic medicament. In particular, said Harderian lipid compound-containing vehicle is used to deliver any desired therapeutic agent, or combination of therapeutic agents, including an antibiotic agent, an antiviral agent, an antifungal agent, an anti-cancer agent, an antiglaucoma agent, an antiinflammatory agent, an analgesic, an immunomodulatory agent, a macro-molecule, or a mixture thereof.

Therapeutic agents that are used in the method of the present invention include, but are not limited to NMDA antagonists, antihistamines, antiparasitics, miotics, sympathomimetics, anticholinergics, local anesthetics, amoebicidals, trichomonocidals, mydriatics, carbonic anhydrase inhibitors, ophthalmic diagnostic agents, ophthalmic agents used as adjuvants in surgery, chelating agents, antineoplastics, diagnostics, adrenergic anesthetics, beta blockers, alpha-2-agonists, cycloplegics, prostaglandins, ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciproflaxin, etc.; sulfonamides such as chloramine T; and sulfones such as sulfanilic acid as the hydrophilic entity, anti-viral drugs, e.g. acyclovir, gancyclovir, vidarabine, azidothymidine, dideoxyinosine, dideoxycytosine, dexamethasone, ciproflaxin, water soluble antibiotics, such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, keterolac, naproxen, etc., an anesthetic, e.g. lidocaine; .beta.-adrenergic blocker or .beta.-adrenergic agonist, e.g. ephidrine, epinephrine, etc.; aldose reductase inhibitor, e.g. epalrestat, ponalrestat, sorbinil, tolrestat; antiallergic, e.g.

cromolyn, beclomethasone, dexamethasone, and flunisolide; colchicine; antiamebic agents, e.g. chloroquine and chlortetracycline; and antifungal agents, e.g. amphotericin, etc., anti-angiogenesis compounds such as anecortave acetate, anti-glaucoma agents, such as brimonidine, acetozolamide, bimatoprost, Timolol, mebefunolol; memantine; alpha-2 adrenergic receptor agonists; 2ME2; anti-neoplastics, such as vinblastine, vincristine, interferons; alpha., beta. and .gamma., antimetabolites, such as folic acid analogs, purine analogs, and pyrimidine analogs; immunosuppressants such as azathiprine, cyclosporine and mizoribine; miotic agents, such as carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like, including derivatives thereof and mixtures thereof.

The present invention is not to be limited in scope by the exemplified embodiments, which are only intended as illustrations of specific aspects of the invention. Although there is described hereinabove a specific method of treating dry eye with compounds obtained from Harderian gland secretions in accordance with the present invention for the purpose of illustrating the manner in which the invention can be used to advantage, it will be appreciated that the invention is not limited thereto. For example, the methods and compositions of the present invention may be used to treat other ocular conditions and disorders, especially when the compounds found in Harderian gland secretions are utilized as a vehicle for a therapeutic agent, as described above. Accordingly, any and all variations and modifications which may occur to those skilled in the art are to be considered to be within the scope and spirit of the invention as defined in the appended claims.

What is claimed is:

1. An ophthalmic vehicle comprising a compound of the formula:

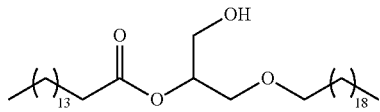

and
said ophthalmic vehicle further comprising at least one additive selected from the group consisting of a buffer, a pH adjustor, and combinations thereof.

2. The ophthalmic vehicle of claim 1, further comprising a therapeutic agent is selected from the group consisting of NMDA antagonists, antibacterials, antihistamines, decongestants, antiinflammatories, antiparasitics, miotics, sympathomimetics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, adrenergic anesthetics, beta blockers, alpha-2-agonists, cycloplegics, prostaglandins and derivatives thereof.

* * * * *